United States Patent [19]

Nelson

[11] Patent Number: 4,527,556
[45] Date of Patent: Jul. 9, 1985

[54] SUPPORT BRACE

[75] Inventor: Marvin G. Nelson, North Branch, Minn.

[73] Assignee: Nelson's Upholstery, Inc., North Branch, Minn.

[21] Appl. No.: 523,681

[22] Filed: Aug. 16, 1983

[51] Int. Cl.³ .............................................. A61F 3/00
[52] U.S. Cl. .................................. 128/80 H; 128/166
[58] Field of Search .......................... 128/80 H, 166

[56] References Cited

U.S. PATENT DOCUMENTS

| | | | |
|---|---|---|---|
| 660,885 | 10/1900 | Brauer | 128/166 |
| 1,231,332 | 6/1917 | Collis | 128/166 |
| 4,280,488 | 7/1981 | Polsky et al. | 128/80 H |
| 4,323,058 | 4/1982 | Detty | 128/80 H |

Primary Examiner—John D. Yasko
Attorney, Agent, or Firm—Merchant, Gould, Smith, Edell, Welter & Schmidt

[57] ABSTRACT

An ankle support (10) for use in supporting an ankle bone and ankle joint is disclosed. The ankle support (10) includes first and second flexible portions (11) and (12). Each of the flexible portions include a first section (20) having a top (22), bottom (23), front side (24) and back side (25) and outer and inner surfaces (26) and (27). A second section (30a) having a front side (34) is cooperatively connected to the first section (20a). A third section (40a) having a front side (34) is cooperatively connected to the second section (30a), defining an open top pouch. The bottom of the second section (30a) proximate to the bottom of the first section (20a) are cooperatively connected. An elastic member (52) having a first edge (52a) and second edge (52b) is provided. The first edge (52a) is cooperatively connected to the back side (25) of the first section (20a) of the first portion (11) and the second edge (52b) is cooperatively connected to the back side of the first section (20b) of the second portion (12), whereby the first and second portions (11) and (12) are cooperatively connected along their back sides and have a distance between them that may vary depending on the amount of elasticity of the elastic member.

26 Claims, 7 Drawing Figures

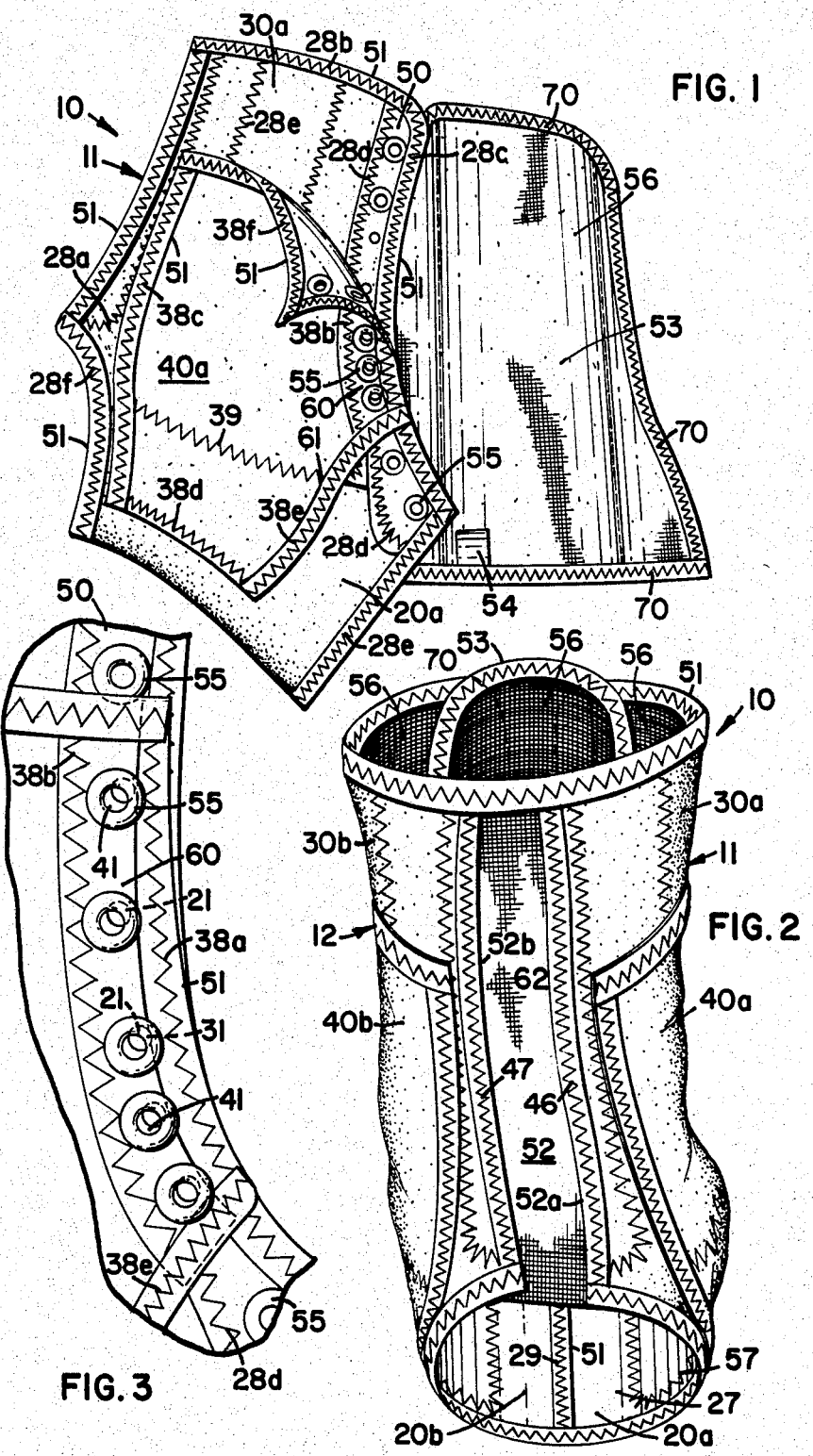

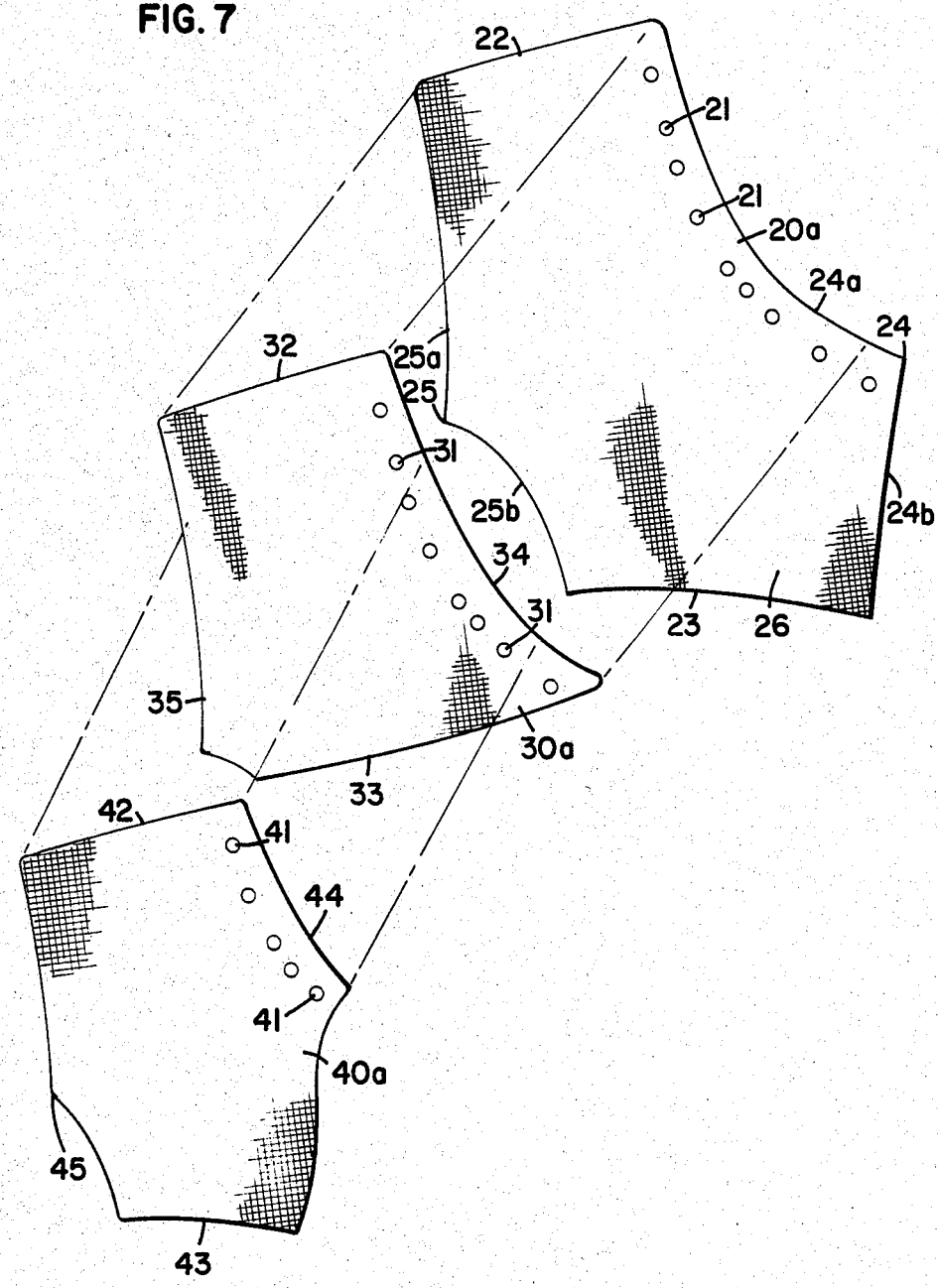

SUPPORT BRACE

FIELD OF THE INVENTION

This invention relates generally to support braces, and more particularly to ankle support braces that may be used for both athletic and medical purposes.

DESCRIPTION OF THE PRIOR ART

Providing ankle support for athletes engaging in various sporting activities is well-known. This protection supports the ankle in such a manner to lock the heel against turning, as this may cause the ankle to be strained or sprained. Various forms of protection are used to both prevent injuries in addition to providing protective support for ankles that have already been injured.

Locking the heel in place and supporting the ankle has been done in a variety of manners. One such method is to use adhesive tape to securely tape the ankle. This is done in a "figure 8" pattern. There are a number of disadvantages in using tape. One of the major disadvantages is the large cost that is associated with taping an ankle each day. Other disadvantages include slippage when the wearer perspires, the development of calluses on the foot and ankle and having to clean the ankle or foot after the tape is removed. Elastic bandages have also been used, but these do not provide as much support as the adhesive tape.

In addition, support has been provided by various types of support braces. One example of such a brace is found in U.S. Pat. No. 4,237,874 issued Dec. 9, 1980 to Ronald E. Nelson. The brace includes a base that is wrapped around the foot and laced up the front. A flexible upright support member is secured to each side of the base and resilient stifening ribs are located in a pluarlity of pockets that are formed in the upright side support member. The ribs straddle the ankle bone. A flexible intermediate transverse member is secured to each side of the upright support members in the vicinity of the ankle bone to provide additional support.

The present invention addresses the disadvantages found in the prior art. In addition, the present invention provides for several improvements over the prior art so as to provide for an improved athletic support brace. In addition, the present invention may be used for a medical support by doctors as a mobile cast.

SUMMARY OF THE INVENTION

The present invention comprises an ankle support for use in supporting an ankle bone and ankle joint. The ankle support includes first and second flexible portions, each of the flexible portions having first, second and third sections. The first section has a top, bottom, front side and back side and outer and inner surfaces. The second section has a front side and the second section is cooperatively connected to the first section. The third section has a front side and the third section is cooperatively connected to the second section, defining an open top pouch. Means are provided for cooperatively connecting the bottom of the second section proximate to the bottom of the first section. An elastic member, having a first edge and second edge is provided. The first edge is cooperatively connected to the back side of the first section of the first portion and the second edge is cooperatively connected to the back side of the first section of the second portion, whereby the first and second portions are cooperatively connected along their back sides and have a distance between them that may vary depending upon the amount of elasticity of the elastic member.

In a preferred embodiment, the first and second flexible portions further comprise means for forming a pocket between the first and second sections and a resilient means carried in the pocket.

In a preferred embodiment, the open top pouch is adapted to receive either an ice pack or a brace.

BRIEF DESCRIPTION OF THE DRAWINGS

FIG. 1 is a side elevational view of the support brace incorporating my present invention;

FIG. 2 is a perspective view, viewed generally from the back and above of the support brace of FIG. 1;

FIG. 3 is an enlarged view of a section of the support brace of Figure showing the relationship of the lace openings;

FIG. 7 is an exploded view showing the relationship of the three major sections of one side of the support brace of FIG. 1.

DESCRIPTION OF THE PREFERRED EMBODIMENT

Figure 4:
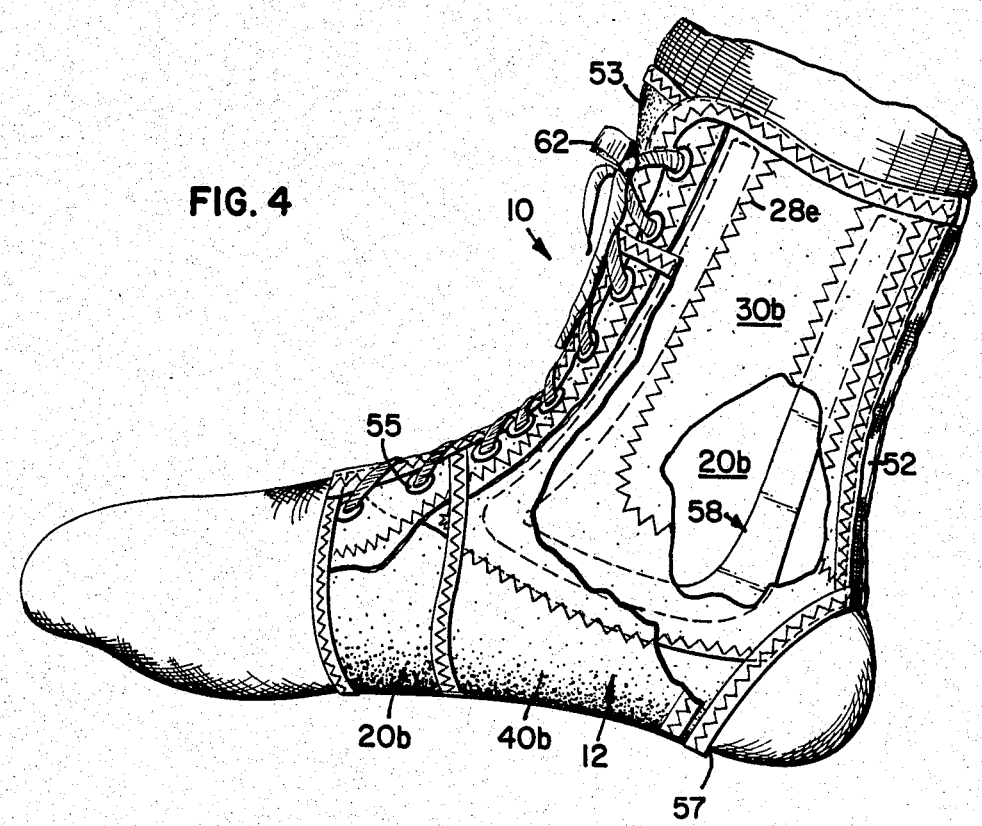
FIG. 4 is a side elevational view of the support brace of FIG. 1 on a foot, with portions of the support brace broken away.
Figure 5:
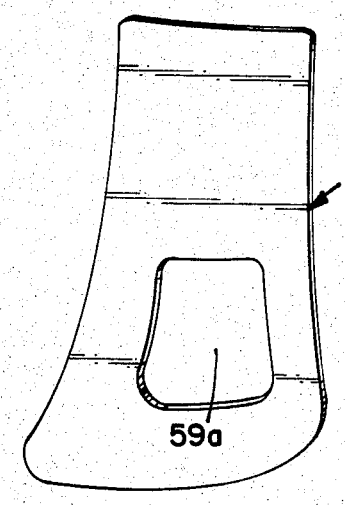
FIG. 5 is a perspective view of a brace insert that may be used with the support brace of FIG. 1.

Referring to the drawings, wherein like numerals represent like parts throughout the several views, there is generally designated at 10 an ankle support. The ankle support 10 includes a first flexible portion 11 and a second flexible portion 12. The first flexible portion 11 includes a first section 20a, second section 30a and third section 40a. The second flexible portion 12 includes a first section 20b, second section 30b and third section 40b. The first flexible portion 11 and second flexible portion 12 are identical to each other, except for the fact that they are a mirror images of one another. Therefore, due to the similar construction, the following is a detailed description of how the first flexible portion 11 is constructed, it being understood that the second flexible portion 12 is similarly constructed with similar components.

In FIG. 7, an exploded view of the first section 20a, second section 30a and third section 40a is shown. As will be more fully discussed hereinafter, these three sections are cooperatively connected to form the first flexible portion 11. The first section 20a has a top 22, bottom 23, front side 24 and back side 25. The front side 24 includes a first portion 24a having a generally concaved shape and a second portion 24b being generally straight. The back side 25 includes a first section 25a that is generally straight except for a slight curve outward toward the middle to accommodate the curve of the wearer's foot and a curve second portion 25b that forms a portion of a heel opening 57, to be described more fully hereafter. A plurality of openings 21 are spaced along the front side 24a to provide opening through which laces may be laced. The first section 20a has an outer surface 26 and an inner surface 27. Padding 56 is cooperatively connected to the inner surface 27.

The second section 30a is cooperatively connected to the outer surface 26 of the first section 20a. The second section 30a has generally the same size as the first section 20a except is it is shorter in length. The second section 30a has a top 32, bottom 33, front side 34 and back side 35. A plurality of openings 31 are provided along the front side 34. When the second section 30a is cooperatively connected to the first section 20a, the openings 31 are in alignment with the openings 21. Before the second section 30a is connected to the second section 20a, a stirrup 38 is placed between the first section 20a and second section 30a. The second section 30a is then cooperatively connected to the first section 20a by appropriate means, such as stitching. A binding 51 may also be used when the first and second sections are connected. The binding 51 provides for additional strength and comfort. As clearly shown in FIG. 1, the first section 20a is cooperatively connected to the second section 30a along the back side by stitching 28a, and 28f along the top by stitching 28b and front side by stitching 28c. The binding 51 is connected to the first and second sections 20a and 30a by stitching 28a through 28e.

Figure 6:
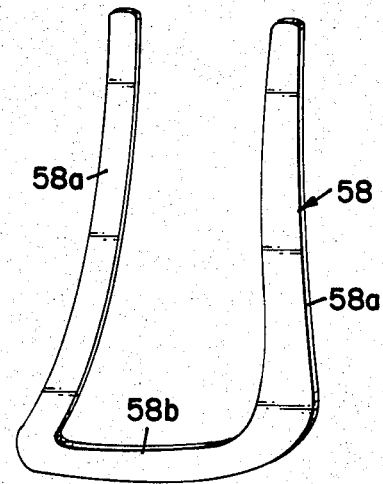
FIG. 6 is a perspective view of the stirrup of the support brace as shown in FIG. 4.

As shown in FIG. 1, a reinforcing strip 50 may also be used. The reinforcement strip 50 is cooperatively connected to the second section 30a and is secured by stitching 28c and 28d. The stitching 28a, 28b and 28d forms a pocket into which the stirrup 50a is positioned. As can be seen in FIG. 6, the stirrup 58 is of a general U-shaped construction having two upright sections 58a and a bottom connecting section 58b. As more clearly shown in FIG. 4, the stirrup 58 is positioned in a pocket between the outer surface 26 of the first section 20a and the second section 30a. Stitching 28e further connects the first section 20a to the second section 30a and follows generally the inside of the stirrup 58. The stirrup 58 is positioned to surround the ankle bone on the sides and bottom. This provides more protection and support than simply straddling the ankle bone as in prior art supports. Eyelets 55 are cooperatively connected to the top and bottom openings 21 and 31.

The third section 40a is cooperatively connected to the second section 30a, defining an open top pouch. The third section 40a has a top 42, bottom 43, front side 44 and back side 45. A plurality of openings 41 are provided along the front side 44 of the third section 40a. A reinforcing strip 60 is cooperatively connected to the front side 44 and a plurality of eyelets 55 are cooperatively connected through the openings 41. A binding 51 is cooperatively connected to the top 42 by stitching 38f. Binding 51 is cooperatively connected to the front side 44 by stitching 38a. The stitching 38a is also used to connect the reinforcing strip 50. Reinforcement strip 60 is also connected to the third section by means of stitching 38b. The back side 45 is cooperatively connected to the second section 30a by means of stitching 38c. The stitching 38c also is used to connect the binding 51. The bottom 43 is connected to the second section 30a by stitching 38d. The lower portion of the front side 44 is connected to the second section 30a by stitching 38e. However, the stitching 38e above point 61 is used to only connect the binding 51 to the third section 40a and does not connect the third section 40a to the second section 30a. Stitching 39 likewise connects the second section 30a to the third section 40a. Stitching 39 defines a lower portion of the open top pouch. Therefore, it can be seen, that the top 42, and front side 44 to point 61 is not connected to the second section 30a. This therefore defines an open top pouch which will have a number of uses that will be more fully described hereinafter. The stitching 39 is also over the bottom 33 of the second section 30a and may be used to secure the bottom 33 to the first section 20a.

A tongue member 53 is also provided. The tongue section 53 may be cooperatively connected to either the flexible portion 11 or 12. As shown in FIG. 1, the tongue 53 is cooperatively connected to the first section 20a by means of the lowermost part of stitching 28d. A loop 54 is provided in the tongue member 53 through which lacing may be inserted. Padding 56 is cooperatively connected to the inner surface 27 of the first section 20 by stitching 28d, 28c, 28e and 28f and to the inner surface of the tongue 53 by stitching 70. The padding 56 will provide for additional support and compression when the support brace is secured to a wearer's foot.

The bottom 23 of the first section 20a is connected to the bottom of the second section 20b by means of stitching 29. This connection may likewise be reinforced by a binding 51.

The back side of the first flexible portion 11 is cooperatively connected to the back side of the second flexible portion 12 by means of an elastic member 52. The elastic member 52 has a first edge 52a and a second edge 52b. The first edge 52a is cooperatively connected to the back side 25 of the first section 20a of the first flexible portion 11 by stitching 46 and the second edge 52b is cooperatively connected to the back side of the first section 20b of the second flexible portion 12 by means of stitching 47. In a preferred embodiment, the elastic member 52 is connected such that the back sides are separated by a distance of from 1/16 to ¼ inch. Further, the elastic member stretches to allow this separation to increase up to ½ to ¾ inch.

A binding 51 may be also used along stitching 46 and 47.

As can be seen in FIG. 3, the openings 41 are offset from the openings 31 and 21 generally downward and away from the front side. While the amount of offset may vary, it has been found that an offset of approximately 1/32 to 1/16 of an inch is preferable. In use, the ankle support 10 is placed on the foot of a wearer by inserting the heel into a heel opening 57 that is defined by the edge 25b of the first section 20a and first section 20b. The toes would extend out the straight side 24b of front side 24. Laces 62 are then inserted through the bottom two eyelets 55 of the second section 30a. As the ankle support 10 is continued to be laced up, the laces would then go through the lowest eyelet 55 in the third section and a corresponding offset in the opening 31 in the second section 30a. The continued lacing through the openings 41 will flatten the third section 40a against the second section 30a. The laces are then pulled to the desired tightness to support the ankle. The offset holes 41 provide for extra support for the ankle. By having the holes 41 slightly offset from the corresponding openings 31, when the laces are tightened, the third section 40a is brought up and across while tightening. This more closely simulates the figure 8 taping of adhesive tape and provides the additional advantages of the figure 8 taping. In addition, the padding 56 acts as a compress and allows for further compression and support for the ankle.

The elastic member 52 allows for a smaller heel opening 57 by allowing the ankle support 10 to be laced tighter, provides a better heel lock and still give the required mobility without a cutting action into the wearer's foot or ankle.

The first section, second section and third sections may be made from any appropriate material such as a combination nylon and polymesh covered with a vinyl coating. The binding may also be made of any suitable material such as herculite material, available from the Herculite Corporation in New York. The stirrup 58 and brace 59 may be made of any resilient material. In a preferred embodiment, the material is a ¼ inch thick polyethylene plastic.

When the ankle support 10 is laced, the third section 40a is flush with the second section 30a. However, upon receiving an injury, it is often advantageous to apply ice to the injury and at the same time maintain support on the ankle. With the open top pouch, it is simply a matter of loosening the lace to provide a pouch into which an ice pack or similar cold body may be introduced. After the ice pack is inserted in the open pouch, the support brace may be laced and tightened, thereby supplying support and a cold pack at the same time. High density foam may be added to open pouch for a compose and added protection.

In addition, it has been found that the ankle support 10 may be used as a mobile cast when brace 59 is inserted in the open top pouch. The brace 59 is made of a suitable resilient material, such as a polyethylene plastic. This provides the necessary stiffness with still allowing for flexibility. The brace 59 has an opening 59a which, when positioned in the open top pouch, surrounds the ankle bone. The ankle support with the brace 59, may then be used as a mobile cast by doctors. It has been found that the recovery time is faster when using the ankle support 10 and brace 59 as compared to a solid cast, because there is less loss of muscle tone.

Other modifications of the invention will be apparent to those skilled in the art in light of the foregoing description. This description is intended to provide specific examples of individual embodiments which clearly disclose the present invention. Accordingly, the invention is not limited to these embodiments or to the use of elements having specific configurations and shapes as presented herein. All alternative modifications and variations of the present invention which follows in the spirit and broad scope of the appended claims are included.

I claim:

1. An ankle support for use in supporting an ankle bone and ankle joint, comprising:
   (a) first and second flexible portions, each of said flexible portion comprising:
       (i) a first section having a top, bottom, front side and a back side and outer and inner surfaces;
       (ii) a second section having a front side, said second section cooperatively connected to said first section; and
       (iii) a third section having a front side, said third section cooperatively connected to said second section, defining an open top pouch.
   (b) means for cooperatively connecting said bottom of said second section proximate to said bottom of said first section;
   (c) an elastic member having a first edge and second edge, said first edge cooperatively connected to said back side of said first section of said first portion and said second edge cooperatively connected to said back side of said first section of said second portion, whereby said first and second portions are cooperatively connected along their back sides and have a distance between them that may vary depending on the amount of elasticity of said elastic member;
   (d) a plurality of spaced apart openings formed in said front sides of said first, second and third sections, adapted to receive a lacing laced through said openings to secure said front sides in a closed position; and
   (e) wherein said openings in said first and second sections are aligned and corresponding openings in said third section are offset from said openings in said first and second sections generally downward and away from said front side, whereby when the lacing is tightened, said openings in said third section being offset causes said third section to be pulled up and over toward said front side.

2. The ankle support of claim 1, wherein said first and second flexible portions further comprise:
   (a) means for forming a pocket between said first and second sections; and
   (b) resilient means carried in said pocket.

3. The ankle support of claim 2, wherein said pocket is generally U-shaped.

4. The ankle support of claim 2, wherein said pouch is adapted to receive an ice pack.

5. The ankle support of claim 2, wherein said pouch is adapted to receive a brace.

6. The ankle support of claim 2, wherein said resilient means is a generally U-shaped stirrup having an open top and closed bottom, said stirrup positioned in said pocket so as to fit around the ankle bone.

7. The ankle support of claim 1, further comprising a tongue member having an inner surface and an outer surface, said tongue member cooperatively connected to one of said flexible portions.

8. The ankle support of claim 1, wherein said second sections have top, bottom and back sides and said third sections have top, bottom and back sides, and said ankle support further comprising a binding cooperatively connected to said top, bottom front side and back sides of said first and second sections.

9. The ankle support of claim 10, further comprising a binding cooperatively connected to said top, front side and back side of said third section.

10. The ankle support of claim 1, further comprising padding cooperatively connected to said inner surface of said tongue and said inner surface of said first sections.

11. An ankle support for use in supporting an ankle bone and ankle joint, comprising:
    (a) first and second flexible portions, each of said flexible portion comprising:
        (i) a first section having a top, bottom, front side and a back side and outer and inner surfaces;
        (ii) a second section having a top, bottom, front side and back side, said second section cooperatively connected to said first section;
        (iii) a third section having a top, bottom, front side and back side, said third section cooperatively connected to said second section, defining an open top pouch;
        (iv) means for forming a pocket between said first and second sections; and
        (v) a generally U-shaped stirrup having an open top and closed bottom, said stirrup positioned in said pocket so as to fit around the ankle bone;
    (b) means for cooperatively connecting said bottom of said second section proximate to said bottom of said first section;

(c) an elastic member having a first edge and second edge, said first edge cooperatively connected to said back side of said first section of said first portion and said second edge cooperatively connected to said back side of said first section of said second portion, whereby said first and second portions are cooperatively connected along their back sides and have a distance between them that may vary depending on the amount of elasticity of said elastic member; and (d) a plurality of spaced apart openings formed in said first sides of said first, second and third sections, adapted to receive a lace through said openings to secure said front sides in a closed position, wherein said openings in said first and second sections are aligned and corresponding openings in said third section are offset from said openings in said first and second section generally downward and away from said front side, whereby when the lacing is tightened, said openings in said third section being offset causes said third section to be pulled up and over toward said front side.

12. An ankle support for use in supporting an ankle bone and ankle joint, comprising:
    (a) first and second flexible portions, each of said flexible portion comprising:
        (i) a first section having a top, bottom, front side and a back side and outer and inner surfaces;
        (ii) a second section having a front side, said second section cooperatively connected to said first section; and
        (iii) a third section having a front side, said third section cooperatively connected to said second section, defining an open top pouch.
    (b) means for cooperatively connecting said bottom of said second section proximate to said bottom of said first section; and
    (c) a plurality of spaced apart openings formed in said first sides of said first, second and third sections, adapted to receive a lace through said openings to secure said front sides in a closed position, wherein said openings in said first and second sections are aligned and corresponding openings in said third section are offset from said openings in said first and second section generally downward and away from said front side, whereby when the lacing is tightened, said openings in said third section being offset causes said third section to be pulled up and over toward said front side.

13. The ankle support of claim 12, wherein said first and second flexible portions further comprise:
    (a) means for forming a pocket between said first and second sections; and
    (b) resilient means carried in said pocket.

14. The ankle support of claim 13, wherein said pocket is generally U-shaped.

15. The ankle support of claim 12, wherein said pouch is adapted to receive an ice pack.

16. The ankle support of claim 12, wherein said pouch is adapted to receive a brace.

17. The ankle support of claim 15, wherein said resilient means is a generally U-shaped stirrup having an open top and closed bottom, said stirrup positioned in said pocket so as to fit around the ankle bone.

18. A mobile cast for use in conjunction with an injured ankle, said cast comprising:
    (a) first and second flexible portions, each of said flexible portion comprising:
        (i) a first section having a top, bottom, front side and a back side and outer and inner surfaces;
        (ii) a second section having a front side, said second section cooperatively connected to said first section;
        (iii) a third section having a front side, said third section cooperatively connected to said second section, defining an open top pouch;
        (iv) means for forming a pocket between said first and second sections; and
        (v) a brace having an opening, said opening positioned so as to surround an ankle bone when in use;
    (b) means for cooperatively connecting said bottom of said second section proximate to said bottom of said first section;
    (c) an elastic member having a first edge and second edge, said first edge cooperatively connected to said back side of said first section of said first portion and said second edge cooperatively connected to said back side of said first section of said second portion, whereby said first and second portions are cooperatively connected along their back sides and have a distance between them that may vary depending on the amount of elasticity of said elastic member; and
    (d) a plurality of spaced apart openings formed in said first sides of said first, second and third sections, adapted to receive a lace through said openings to secure said front sides in a closed position, wherein said openings in said first and second sections are aligned and corresponding openings in said third section are offset from said openings in said first and second section generally downward and away from said front side, whereby when the lacing is tightened, said openings in said third section being offset causes said third section to be pulled up and over toward said front side.

19. An ankle support for use in supporting an ankle bone and ankle joint, comprising:
    (a) first and second flexible portions, each of said flexible portion comprising:
        (i) a first section having a top, bottom, front side and a back side and outer and inner surfaces;
        (ii) a third section having a front side, said third section cooperatively connected to said first section, defining an open top pouch; and
    (b) a plurality of openings formed in said front sides of said first and third sections, adapted to receive a lace through said openings to secure said front sides in a closed position, wherein corresponding openings in said third section are offset from said openings in said first section generally downward and away from said front side, whereby when the lacing is tightened, said openings in said third section being offset causes said third section to be pulled up and over toward said front side.

20. The ankle support of claim 19, further comprising:
    (a) means for forming a pocket cooperatively connected to said first section; and
    (b) resilient means carried in said pocket.

21. The ankle support of claim 20, wherein said pocket is generally U-shaped.

22. The ankle support of claim 20, wherein said resilient means is a generally U-shaped stirrup having an open top and closed bottom, said stirrup positioned in said pocket so as to fit around the ankle bone.

23. The ankle support of claim 19, further comprising a tongue member having an inner surface and an outer surface, said tongue member cooperatively connected to one of said flexible portions.

24. The ankle support of claim 19, wherein said third section, when cooperatively connected to said first section defines an open top pouch.

25. The ankle support of claim 24, wherein said pouch is adapted to receive an ice pack.

26. The ankle support of claim 24, wherein said pouch is adapted to receive a brace having an opening, said opening positioned to surround an ankle bone when in use, wherein said ankle support may be used as a mobile cast.

* * * * *